US010682045B2

(12) United States Patent
Wang et al.

(10) Patent No.: US 10,682,045 B2
(45) Date of Patent: Jun. 16, 2020

(54) WIRELESS CAPSULE ENDOSCOPE AND POWER SUPPLY CONTROL METHOD THEREOF

(71) Applicants: Xinhong Wang, SanDiego, CA (US); Guohua Xiao, Plano, TX (US); Xiaodong Duan, Pleasanton, CA (US); Junjie Wang, Hangzhou (CN)

(72) Inventors: Xinhong Wang, SanDiego, CA (US); Guohua Xiao, Plano, TX (US); Xiaodong Duan, Pleasanton, CA (US); Junjie Wang, Hangzhou (CN)

(73) Assignee: ANKON TECHNOLOGIES CO., LTD, Wuhan (CN)

( * ) Notice: Subject to any disclaimer, the term of this patent is extended or adjusted under 35 U.S.C. 154(b) by 0 days.

(21) Appl. No.: 16/705,251

(22) Filed: Dec. 6, 2019

(65) Prior Publication Data
US 2020/0107709 A1  Apr. 9, 2020

Related U.S. Application Data

(63) Continuation of application No. 14/321,537, filed on Jul. 1, 2014, now Pat. No. 10,531,788.

(51) Int. Cl.
*A61B 1/04* (2006.01)
*A61B 1/045* (2006.01)
(Continued)

(52) U.S. Cl.
CPC .......... *A61B 1/041* (2013.01); *A61B 1/00036* (2013.01); *A61B 1/045* (2013.01);
(Continued)

(58) Field of Classification Search
CPC ..... A61B 1/00036; A61B 1/041; A61B 1/045; A61B 2560/0209; A61B 5/07; A61B 5/076
See application file for complete search history.

(56) References Cited

U.S. PATENT DOCUMENTS

2002/0032366 A1* 3/2002 Iddan ................. A61B 1/00036
                                                         600/117
2008/0300459 A1* 12/2008 Kimura ............. A61B 1/00016
                                                         600/118

FOREIGN PATENT DOCUMENTS

CN     102860810 A    1/2013
CN     202843565 U    4/2013
(Continued)

OTHER PUBLICATIONS

Search Report for the counterpart Chinese application by State intellectual property office of the P. R. C, dated May 23, 2014.

*Primary Examiner* — Aaron B Fairchild
(74) *Attorney, Agent, or Firm* — Treasure IP Group, LLC

(57) ABSTRACT

The present invention relates to a wireless capsule endoscope and a power supply control method thereof. The method includes controlling the power supply of the capsule endoscope wirelessly and automatically adjusting power consumption of the power supply in the capsule endoscope. The wireless capsule endoscope includes a capsule casing, a light generator arranged at outside of the capsule casing, an opto-electronic switching starter arranged in the capsule casing, a power supply, a control module, a posture sensor, an illumination unit, an image processing device and a radio frequency transmission unit. The power supply being driven by the light generator in the present invention can effectively solve the incompatible problem between a traditional magnetic switch and a magnetic control device. Meanwhile, the control module and the posture detector enable the power supply to be in different working status under different states, which can prolong the service life of the power supply of the capsule endoscope.

5 Claims, 4 Drawing Sheets

(51) Int. Cl.
  *A61B 1/00* (2006.01)
  *A61B 5/07* (2006.01)
(52) U.S. Cl.
  CPC ................. *A61B 5/07* (2013.01); *A61B 5/076* (2013.01); *A61B 2560/0209* (2013.01)

(56) References Cited

FOREIGN PATENT DOCUMENTS

| | | |
|---|---|---|
| JP | P2004-645 A | 1/2004 |
| JP | P2004358094 A | 12/2004 |
| JP | P2005-552 A | 1/2005 |
| JP | P2005-73885 A | 3/2005 |
| JP | P2009-189742 A | 8/2009 |

\* cited by examiner

WIRELESS CAPSULE ENDOSCOPE AND POWER SUPPLY CONTROL METHOD THEREOF

CROSS REFERENCE TO RELATED APPLICATION

This application claims priority to Chinese Application No. 201310275948.3, filed on Jul. 3, 2013. Chinese Application is incorporated herein by reference in its entirety.

FIELD OF INVENTION

The present invention relates to a wireless capsule endoscope and a power supply control method thereof, and more particularly to a positionable wireless capsule endoscope which can efficiently and flexibly take images of an interior of a digestive tract and the power supply control method thereof.

BACKGROUND

Capsule endoscopy is booming and highly recognized in the international medical device field mainly because it has become an effective method for diagnosis of gastrointestinal diseases. A capsule endoscope comprises an imaging unit with solid state imaging element, a LED illumination unit, a wireless communication unit and other components all of which are incorporated in a capsule enclosure of a size suitable to be taken orally. After being swallowed by a subject, this capsule endoscope travels through the gastrointestinal (GI) tract of the subject while capturing images of the stomach or intestine and transmitting the images to an external data recorder through the wireless communication unit. The images can be displayed on a display screen. Based on the image information, the physician can make a diagnosis of gastrointestinal diseases for the subject in a painless and non-invasive state.

In order to make the capsule endoscope more flexible, controllable and more efficient, many foreign researchers have proposed to change the traditional capsule endoscope passively driven by digestive tract peristalsis to an actively-driven one. For example, PCT patent publication No. 01/35813 discloses a controllable capsule endoscope, which is controlled by driving the components of the capsule endoscope thereof. The capsule endoscope incorporates a reed switch. Said reed switch remains off under a certain intensity of magnetic field applied by an external magnetic device and is on when the intensity of the magnetic field is declined. Therefore, an effective navigation control of the capsule endoscope can be achieved by applying the magnetic field to the capsule endoscope to supply power to each constituent component. However, due to the use of the external magnetic device, any other magnetic components inside the capsule endoscope will have interference. Additionally, after the capsule endoscope is taken out of the package, it will take a certain period of time before being swallowed by the subject. During this wait period of time, the functions of the capsule endoscope remain active, so this is a problem because much power is wasted. For such a capsule endoscope with limited power supply, the waste of power may greatly affect the diagnosis. Besides, because of the influence of the magnetic field, it is difficult to solve the waste problem of the electrical power for the capsule endoscope with many magnetic components.

In order to use an external magnetic control system or any other magnetic components for positioning capability, a power control means other than a magnetic switch must be used. Thus, a RFID switch can become adopted. The wireless switch control method turns on the internal power supply of the capsule endoscope using an external start command. However, a big receiving antenna is required when RFID switch is used to control the power supply, which is difficult to achieve for a capsule endoscope with limited internal space.

SUMMARY OF THE INVENTION

The present invention includes a wireless capsule endoscope and a power supply control method thereof, which can effectively avoid the sometime conflicting requirement between the traditional magnetic switch and the magnetic control device by starting the power source with a light generator outside the capsule endoscope, and meanwhile can prolong the battery life of the capsule endoscope by using a control module and a posture sensor which enable the battery to be in different power supply status under different conditions.

In one embodiment, the present invention provides a wireless capsule endoscope which comprises a LED illumination unit, an image processing unit, a radio frequency transmission unit and a power supply; and further comprises an optoelectronic switch starter, a control module, a posture sensor and an external light generator. The optoelectronic switch starter and the LED illumination unit are mounted on a disc-shaped circuit board with through holes. The power supply is arranged between the image processing unit and the radio frequency transmission unit, and the control module and the posture sensor are arranged between the power supply and the radio frequency transmission unit.

Further, the power supply is composed of silver oxide batteries and a power control board.

Further, the control module is a digital signal processing unit provided for information processing, comprising a circuit module composed of electronic components such as chip resistors and chip capacitors, which has a function of voltage control.

Further, the posture sensor is a gravity sensor.

Further, the light generator is composed of photodiodes.

In another embodiment, a power supply control method of the wireless capsule endoscope is also disclosed, which comprises using an external wireless control to turn on the power supply of the capsule endoscope and an automatic adjustment inside the capsule endoscope to control the consumption of the power supply. When the power supply is needed to be turned on, the external light generator generates an infrared light beam of certain intensity which shines on the optoelectronic switch starter provided at interior of the capsule endoscope, and the optoelectronic switch starter converts the light signal to an electrical signal and generates a pulse to start an electronic switch of the optoelectronic switch starter, making the internal power supply circuit of the capsule endoscope closed, and maintaining components of the capsule endoscope inside the capsule endoscope in a state of low power consumption. When the capsule endoscope with the power supply turned on is located in a body cavity, an internal control module adjusts the battery output power according to posture information of the capsule detected by the posture sensor, so that the capsule endoscope has power output in an effective working condition, or the capsule endoscope controls the components of the capsule endoscope to run with low power consumption mode in an ineffective working condition.

Further, the wavelengths of the infrared light beam generated by the external light generator is 780 nm-880 nm.

Further, the low power consumption mode means a non-power consumption state when the capsule endoscope stops taking images and just transmits image information. The effective working condition means an operating state of the capsule endoscope at a diseased region of the body cavity where the position of the capsule endoscope is changing and the images taken by the capsule endoscope are not duplicated. The ineffective working condition means an operating state of the capsule endoscope is in regions of no interest including when the capsule is just being swallowed and has not arrived at a diseased region (for example stomach, small bowel), departure from a diseased region, or at a diseased region but the capsule endoscope has completed taking images and it is in state of transmitting images at the same position.

The wireless capsule endoscope and the power supply control method disclosed herein solve the problem that the magnetic switch used in the traditional capsule endoscope is incompatible with the magnetic control device. The internal optoelectronic switch starter of the capsule endoscope is turned on by the external photoelectric generator. When the capsule endoscope is located in the body cavity, the operating state of internal components of the capsule endoscope of the capsule endoscope is changed by the power supply and the control module, thereby prolonging the battery life. This greatly improves the flexibility and effectiveness of the capsule endoscope and has created important application value in the basic examination of digestive tract.

BRIEF DESCRIPTION OF THE DRAWINGS

The components in the drawing are not necessarily drawn to scale, the emphasis instead being placed upon clearly illustrating the principles of the described embodiments. In the drawings, reference numerals designate corresponding parts throughout various views, and all the views are schematic.

DETAILED DESCRIPTION OF EMBODIMENTS

The present invention will now be described more fully hereinafter with reference to the accompanying drawings, in which currently preferred embodiments of the invention are shown. This invention may, however, be embodied in many different forms and should not be construed as limited to the embodiments set forth herein.

(Structural Components of the Capsule Endoscope are Described Below).

Figure 1:
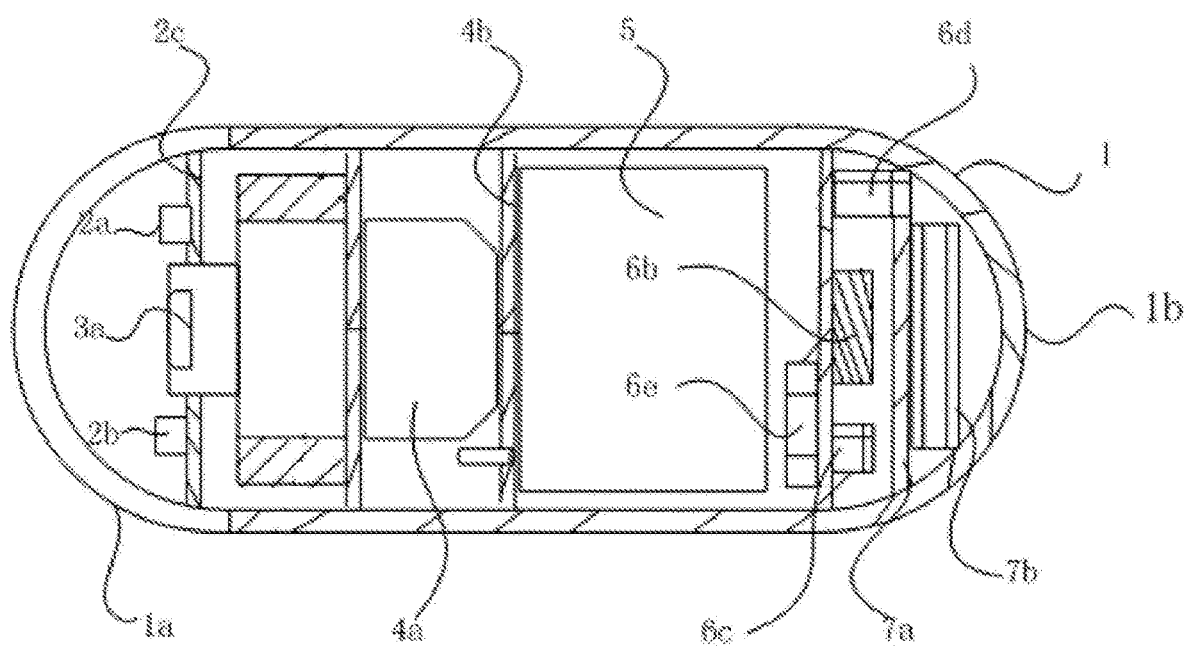
FIG. 1 is a cross-sectional configuration diagram schematically illustrating an internal configuration of a capsule endoscope of the present invention.
Figure 2:
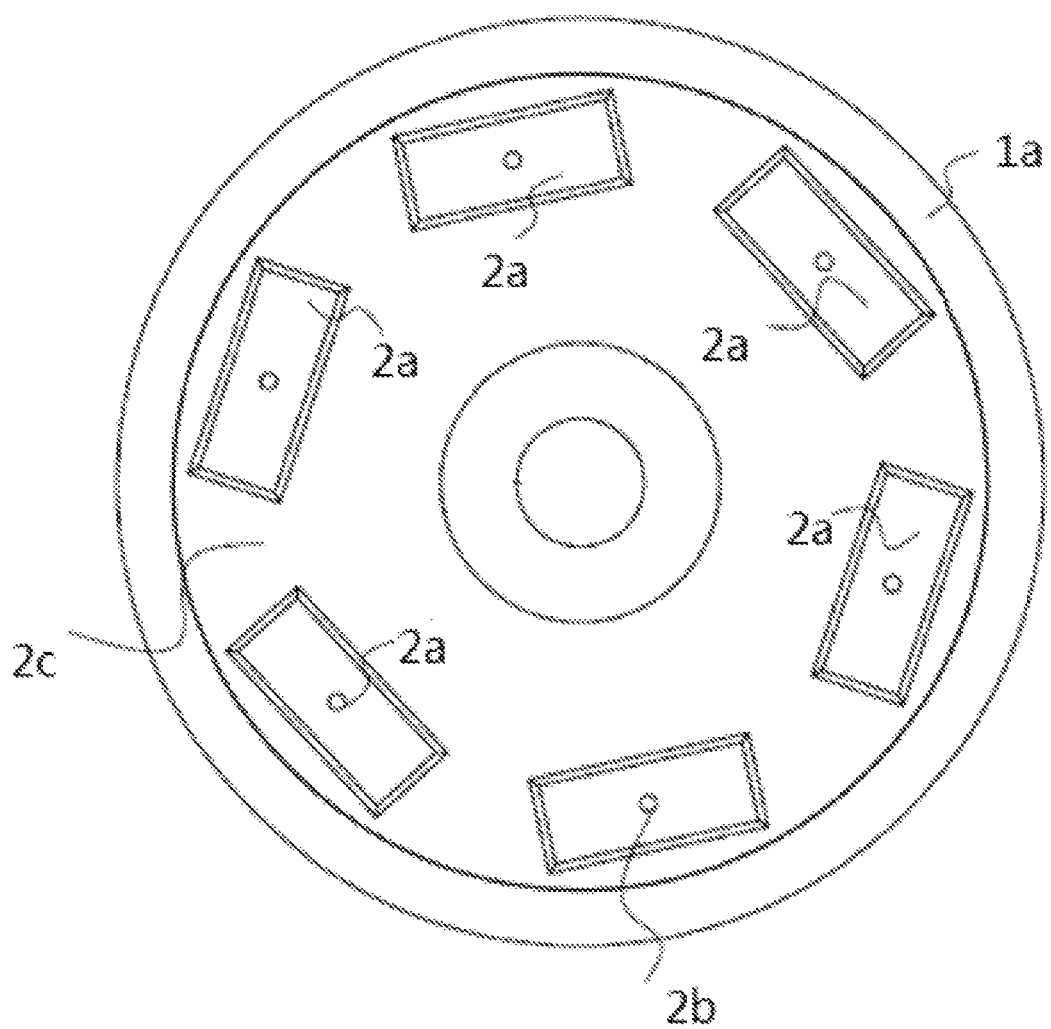
FIG. 2 is a front view of the capsule endoscope.
Figure 3:
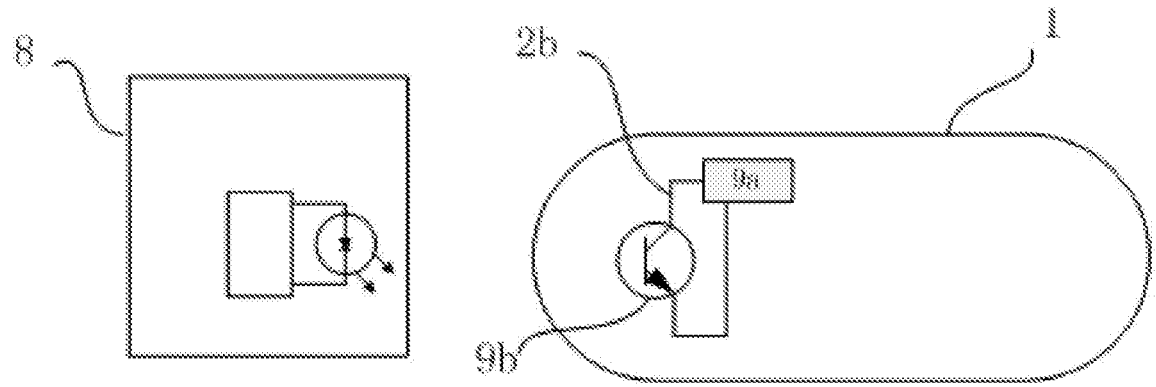
FIG. 3 is a schematic diagram for showing that the power supply of the capsule endoscope is controlled by an external light generator.

Referring to FIGS. 1 to 5, the configuration of a wireless capsule endoscope of the present invention is described. The capsule endoscope disclosed herein comprises a capsule-shaped enclosure 1, a LED illumination unit 2 for illuminating the interior of the digestive tract of a subject, an image processing unit 3 for capturing images of a region illuminated by the LED illumination unit 2 and processing the images, and a radio frequency transmission unit 7 (including a radio frequency circuit board 7a and an antenna 7b) for wirelessly transmitting the images taken in the digestive tract of the subject to the outside. The capsule endoscope further comprises a power supply 4 supplying power to each constituent component of the capsule endoscope, and a control module 6 for controlling the operating state of each constituent component inside the capsule endoscope. The power supply control system for realizing optoelectronic start of the capsule endoscope further includes an external light generator 8 as shown in FIG. 3. The enclosure 1 is composed of a capsule-shaped body 1b and a hemispherical optical dome 1a attached to the front end of the enclosure 1. The hemispherical optical dome 1a is transparent and performs with high light transmission. The LED illumination unit 2 is arranged close to the hemispherical optical dome 1a for efficiently illuminating the interior of the digestive tract. The image processing unit 3 has an optical lens 3a.

(Optoelectronic Switch Operation Principles are Described Below).

Combined with the configuration of the capsule endoscope, the optoelectronic switch operation mechanism is illustrated in this paragraph. The external light generator 8 can generate a light beam of certain intensity under controlled conditions. When the light beam passes through the optically-transparent hemispherical optical dome 1a and received by an optoelectronic switch starter 2b on an illumination circuit board 2c, an electronic switch 9a of the optoelectronic switch starter 2b connecting to a field effect transistor 9b is closed to provide a connection. That is, the optoelectronic switch starter 2b converts an optical signal of the light generator 8 into an electrical signal to generate a turn-on pulse 2e, thereby realizing connection between the power supply 4 and the components of the capsule endoscope inside the capsule endoscope. The components of the capsule endoscope comprise the LED illumination unit 2, the image processing unit 3, the radio frequency transmission unit 7, and a magnetic dipole 5 of the capsule endoscope, etc.

(Special Characteristics of the Present Invention is Described Below).

In order to separate from the spectrum generated by illumination components 2a (for example the LED illumination unit 2), which is configured to generate a light beam at certain intensity for illumination, the light generator 8 and the optoelectronic switch starter 2b inside the capsule endoscope as disclosed herein use photodiodes operable at a wavelength ranging between 780 nm and 880 nm to accomplish conversion from optical signals to electric signals. By doing so, the light generator 8 and optoelectronic switch starter 2b, as a power supply control assembly, effectively avoids the spectral overlap with the visible light, which is used to provide the field view for the optical lens 3a of the image processing apparatus 3.

(Position Description)

As illustrated in FIGS. 1 and 2, similar to the position of the LED illumination unit 2, in order to for light generator 8 to receive a light beam at certain intensity from the outside, the optoelectronic switch starter 2b should be arranged at a position which allows it to receive most light transmission. Therefore, optoelectronic switch starter 2b is disposed at slope side near middle of the optical dome 1a shown in FIG. 2. The plurality of light-emitting devices 2a can be mounted on the annular circuit board 2c with through holes around the image processing apparatus 3, and the light-emitting device 2a is mounted in the vicinity of the outer periphery for illuminating the inside of the digestive tract.

(Power and Module Control Process)

When the electronic switch 9a of the optoelectronic switch starter 2b is turned on, the switch control mode inside the capsule endoscope is established, in this mode, the power control is accomplished by the power supply 4. The power supply 4 comprises one or plural batteries 4a having a predetermined capacity and a power supply board 4b, and the power supply 4 is arranged between the image processing unit 3 and the magnetic dipole 5. The one or plural batteries 4a are mounted on the power control board 4b. The power supply board 4b is connected to each constituent component and supplies power to each constituent component inside the capsule endoscope. The battery 4a comprises two silver oxide button dry batteries.

The power supply 4 enables the capsule endoscope to take images inside the digestive tract and transmit data during an effective working condition, and controls the components of the capsule endoscope in the capsule endoscope to run with a low power consumption mode during an ineffective working condition. When the capsule endoscope is detected by the control module 6 at regions of the body cavity of no interest, or when the capsule endoscope is detected by the control module 6 at the same position as before, the capsule endoscope is indicated to be in the ineffective working condition. The regions of no interests include non-diseased regions, for example, oral cavity.

Figure 4:
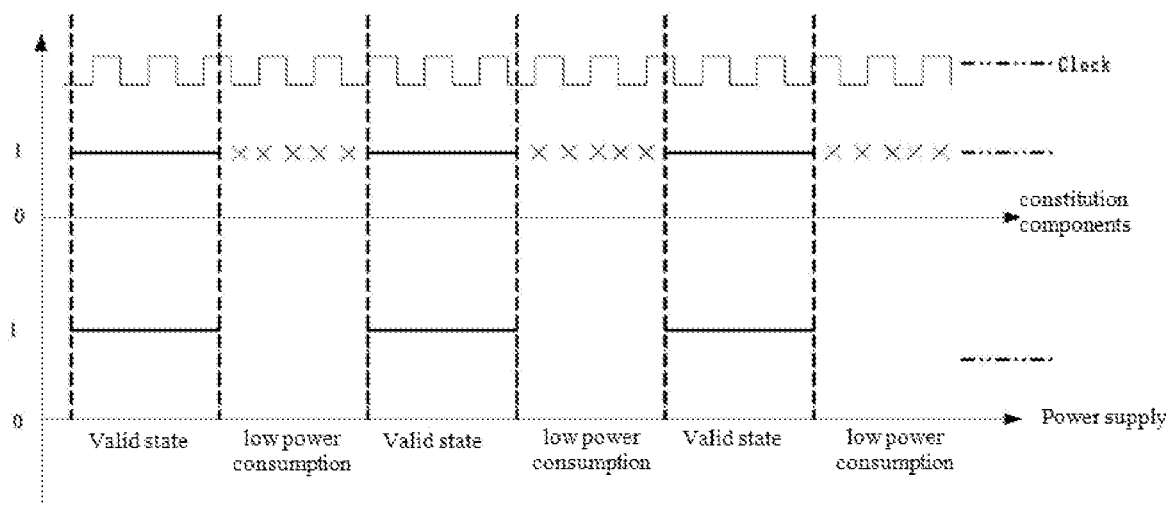
FIG. 4 is a schematic diagram for showing the power supply and control module in different operating states.
Figure 5:
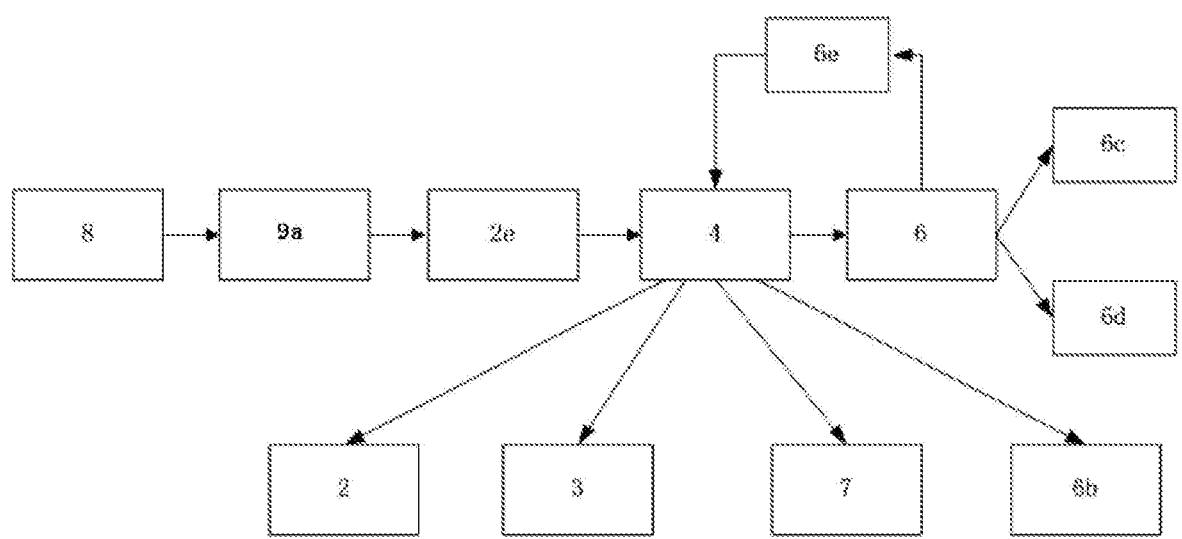
FIG. 5 is a flowchart of the power supply control method of the capsule endoscope.

After receiving the turn-on pulse 2e generated by the electronic switch 9a of the optoelectronic switch starter 2b, the power supply 4 is connected to the circuit of each constituent component inside the capsule endoscope, and the battery 4a supplies power to each constituent component properly. The control module 6 includes a posture sensor 6b, a data processing unit 6c, a calibration unit 6d and a feedback unit 6e. The calibration unit 6d is used for analyzing and calibrating the characteristic of the posture sensor 6b. When it is shown that the capsule endoscope is in the ineffective working condition according to the analysis performed by the calibration unit 6d on the characteristics of the posture sensor 6b and information post-processed by the data processing unit 6c, the feedback unit 6e indicates the power supply 4 to work in the low power consumption mode, thereby reducing power consumption of each constituent component inside the capsule endoscope. If the characteristics information indicated by the posture sensor 6b show that the capsule endoscope is currently in the effective working condition, then the power supply 4 works properly to power each constituent component inside the capsule endoscope. Referring to FIG. 4, a schematic diagram showing the power supply 4 and the control module 6 in different operating states. The square wave signal is a continuous clock signal, and in the superimposed coordinates, the "1" and "0" indicate signal level values, wherein "1" indicates the power supply is supplying power to the components of the capsule endoscope and "0" indicates the power supply is not to supply power and the components of the capsule endoscope are working in a low power consumption mode. The time duration of effective working condition (normal working condition) and low power consumption mode of the components of the capsule endoscope are determined by a control and positioning algorithm. Without the sacrifice of normal image taking and lesion investigation, the power supply system of present invention can supply power to the components of the capsule endoscope when it needs to work, and enable the components of the capsule endoscope to work with the low power consumption mode when the modules does not need to work. Therefore, the components of the capsule endoscope inside the capsule endoscope can work effectively, and thereby save power and extend battery life.

As described above, by using the optoelectronic switching starter 2b, the capsule endoscope of the present invention solves the incompatible problem of the traditional magnetic switch and a magnetic drive device. Besides, the combination of the optoelectronic switching starter 2b, the power supply 4, the control module 6 and the posture sensor 6b enable the capsule endoscope to move more flexibly and be smaller, and the lifetime of the batteries 4a is extended, all of which can improve the performance of the capsule endoscope.

Turning on the power supply actively from outside can be achieved by the wireless capsule endoscope and the power control method in the present invention, which is suitable for the capsule endoscope with magnetic components for improving the performance and extending service lifetime of the capsule endoscope. Meanwhile, the posture sensor 6b and the control module 6 enable the power supply to be in different working status under different s, which can double the service life of the capsule endoscope still maintaining the limited electrical power and limited interior space. The capsule endoscope provided herein is very practical.

It is to be understood, however, that even though numerous characteristics and advantages of preferred and exemplary embodiments have been set out in the foregoing description, together with details of the structures and functions of the embodiments, the embodiments are for illustration purpose only; and that changes may be made in detail within the principles of present disclosure to the full extent indicated by the broadest general meaning of the terms in which the appended claims are expressed.

The invention claimed is:

1. A power supply control method of a wireless capsule endoscope comprising:
   externally and wirelessly controlling a power supply of the capsule endoscope and automatically adjusting power consumption of the power supply in the capsule endoscope; and
   wherein
   before an opto-electronic switching starter receives a light beam from an external light generator, interior components of the capsule endoscope are in a low power status;
   the external light generator generates the light beam, which is of certain intensity and at a wavelength not-overlapping with an emission generated by an illumination unit of the capsule endoscope, and the light beam shining on the opto-electronic switching starter provided in an interior of the capsule endoscope, and the opto-electronic switching starter converting light signals to electrical signals to generate an opening pulse which turns the power supply on,
   said opto-electronic switching starter is mounted together with a plurality of LED illumination units on a disk-shaped illumination circuit board around an image processing unit, next to an optically-transparent hemispherical optical dome; and
   when the power supply is turned on, a control module is configured to adjust the power supply to a low output status or a full output status depending on posture information provided by a posture sensor of the capsule endoscope.

2. The power supply control method as claimed in claim 1, wherein a wavelength of the light beam is 780 nm to 880 nm.

3. The power supply control method as claimed in claim 1, wherein when the power supply is in the low power output status, the capsule endoscope does not photograph nor transmit image information.

4. The power supply control method as claimed in claim 1, wherein when the power supply is in the full output status, the position of the capsule endoscope is changing and images picked up are not duplicated, the capsule endoscope can photograph and transmit image information.

5. The power supply control method as claimed in claim 1, wherein when the capsule endoscope is not located in a region of interest or has completed photographing and transmitting image information, the capsule endoscope is set to the low output status.

* * * * *